(12) United States Patent
Johns et al.

(10) Patent No.: US 6,372,757 B1
(45) Date of Patent: Apr. 16, 2002

(54) PHENYLUREA AND PHENYLTHIO UREA DERIVATIVES

(75) Inventors: Amanda Johns, St Albans; Roderick Alan Porter, Ashwell, both of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/700,002

(22) PCT Filed: May 4, 1999

(86) PCT No.: PCT/EP99/03100

§ 371 Date: Dec. 8, 2000

§ 102(e) Date: Dec. 8, 2000

(87) PCT Pub. No.: WO99/58533

PCT Pub. Date: Nov. 18, 1999

(30) Foreign Application Priority Data

| | | |
|---|---|---|
| May 8, 1998 | (GB) | 9809972 |
| May 8, 1998 | (GB) | 9809988 |
| Feb. 12, 1999 | (GB) | 9903268 |

(51) Int. Cl.[7] ............... A61K 31/435; C07D 471/04
(52) U.S. Cl. ............... 514/300; 514/230.5; 544/105; 546/122
(58) Field of Search .................. 546/122; 544/105; 514/300, 230.5

(56) References Cited

FOREIGN PATENT DOCUMENTS

| CA | 2 222 687 A | 12/1996 |
|---|---|---|
| WO | WO 86/06718 | 11/1986 |
| WO | WO 92/22533 | 12/1992 |
| WO | WO 97/44337 | 11/1997 |
| WO | WO 99/09024 | 2/1999 |

OTHER PUBLICATIONS

Pomorski, et al., Recl. Trav. Chim., 1973, vol. 92, pp. 70–976, Abstact No. XP002114650.
Van Den Haak, et al., Recl. Trav. Chim., 1980, vol. 99, No. 3, pp. 83–86, Abstract No. XP002114651.
Pokorny, et al., J. Heterocycl. Chem., 1972, vol. 9, No. 5, pp. 1151–1153, Abstract No. XP002114652.
Barlin, et al., Aust. J. Chem., 1993, vol. 46, No. 11, pp. 1695–1703, Abstract No. XP002114653.
Wozniak, et al., Liebigs Ann. Chem., 1993, No. 5, pp. 471–475, Abstract No. XP002114654.
Brown, et al., J. Org. Chem., 1971, vol. 36, No. 10, pp. 1331–1335, Abstract No. XP002114655.
McCaustland, et al., J. Hetercycl. Chem., 1970, vol. 7, No. 3, pp. 467–473, Abstract No. XP002114656.
Czuba, et al., Chem. Abstracts, 1980, vol. 92, No. 9, Abstract No. XP002114657.
Czuba, et al., Chem. Abstracts, 1976, vol. 84, No. 17, Abstract No. XP002114658.
Titkova, et al., Chem. Abstracts, 1981, vol. 95, No. 23, Abstract No. XP002114659.
Czuba, et al., Chem. Abstracts, 1992, vol. 117, No. 5, Abstract No. XP002114660.
Wozniak, et al., Chem. Abstracts, 1984, vol. 101, No. 11, Abstract No. XP002114661.
Pomorski, et al., Chem. Abstracts, 1974, vol. 80, No. 17, Abstract No. XP002114662.

*Primary Examiner*—Bernard Dentz
(74) *Attorney, Agent, or Firm*—Kathryn L. Sieburth; Mary E. McCarthy; Charles M. Kinzig

(57) ABSTRACT

Phenyl urea and phenyl thiourea derivatives and their use as pharmaceuticals.

11 Claims, No Drawings

PHENYLUREA AND PHENYLTHIO UREA DERIVATIVES

This is a 371 of International Application PCT/EP99/03100, filed May 4, 1999.

This invention relates to phenyl urea and phenyl thiourea derivatives and their use as pharmaceuticals.

Many medically significant biological processes are mediated by proteins participating in signal transduction pathways that involve G-proteins and/or second messengers.

Polypeptides and polynucletides encoding the human 7-transmembrance G-protein coupled neuropeptide receptor, orexin-1 (HFGAN72), have been identified and are disclosed in EP-A-875565, EP-A-875566 and WO 96/34877. Polypeptides and polynucleotides encoding a second human orexin receptor, orexin-2 (HFGANP), have been identified and are disclosed in EP-A-893498.

Polypeptides and polynucleotides encoding polypeptides which are ligands for the orexin-1 receptor, e.g. orexin-A (Lig72A) are disclosed in EP-A-849361.

Orexin receptors are found in the mammalian host and may be responsible for many biological functions such as pathologies including, but not limited to, depression; anxiety; addictions; obsessive compulsive disorder; affective neurosis/disorder; depressive neurosis/disorder; anxiety neurosis; dysthymic disorder; behavior disorder; mood disorder; sexual dysfunction; psychosexual dysfunction; sex disorder; sexual disorder; schizophrenia; manic depression; delerium; dementia; severe mental retardation and dyskinesias such as Huntington's disease and Gilles de la Tourett's syndrome; feeding disorders such as anorexia, bulimia, cachexia and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adeoma; hypothalamic diseases; Froehlich's syndrome; adrenohypopohysis disease; hypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposima); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; distributed biological and circadian rhythms; and sleep disturbances associated with diseases such as neurological disorders, neuropathic pain and restless leg syndrome; heart and lung diseases; acute and congestive heart failure; hypotension; hypertension; urinary retention; osteoporosis; angina pectoris; myocardial infarction; ischaemic or haemorrhagic stroke; subarachnoid haemmorhage; ulcers; allergies; benign prostatic hypertrophy; chronic renal failure; renal disease; impaired glucose tolerance; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; post-operative pain; neuralgia; conditions associated with visceral pain such as irritable bowel syndrome, migraine and angina; urinary bladder incontinence e.g. urge incontinence; tolerance to narcotics or withdrawal from narcotics; sleep disorders; sleep apnea; narcolespy; insomnia; parasomnia; jet-lag syndrome; and neurodegenerative disorders including nosological entities such as disinhibition-dementia-parkinsonism-amyotrophy complex; pallido-ponto-nigral degeneration, epilepsy and seizure disorders.

Experiments have shown that central administration of orexin-A stimulates food intake in freely-feeding rats during a 4 hour time period. This increase is approximately four-fold over control rats receiving vehicle. These data suggest that orexin-A may be an endogenous regulator of appetite. Therefore, antagonists of orexin receptors may be useful in the treatment of obesity and diabetes, see Cell, 1998, 92, 573–585.

Rat sleep/EEG studies have also shown that central administration of orexin-A causes a does-related increase in arousal, largely at the expense of a reduction in paradoxical sleep and slow wave sleep 2, when administered at the onset of the normal sleep period. Therefore, antagonists of orexin receptors may be useful in the treatment of sleep disorders including insomnia.

The present invention provides phenyl urea and phenyl thiourea derivatives which are non-peptide antagonists of human orexin receptors, in particular orexin-1 receptors. In particular, these compounds are of potential use in the treatment of obesity, including obesity observed in Type 2 (non-insulin-dependent) diabetes patients, and/or sleep disorders.

International Patent Application PCT/GB98/02437 (published after the priority date of the present application) discloses various phenyl urea derivatives as orexin receptor antagonists.

According to the invention there is provided a compound of formula (I):

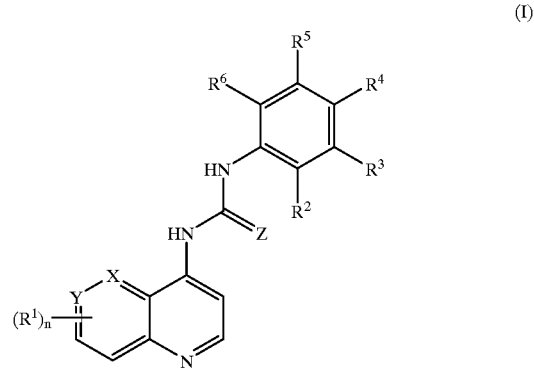

in which:
one of X and Y is N and the other is CH;
Z represents oxygen or sulphur;
$R^1$ represents $(C_{1-6})$alkyl, $(C_{2-6})$alkenyl or $(C_{1-6})$alkoxy, any of which may be optionally substituted; halogen, $R^7CO$— or $NR^8R^9CO$—;
$R^2$, $R^3$, $R^4$, $R^5$ and $R^6$ independently represent $(C_{1-6})$alkyl, $(C_{2-6})$alkenyl, $(C_{1-6})$alkoxy or $(C_{1-6})$alkythio, any of which may be optionally substituted; hydrogen, halogen, nitro, cyano, aryloxy, aryl$(C_{1-6})$alkyloxy, aryl $(C_{1-6})$alkyl, $R^7CO$—, $R^7SO_2NH$—, $R^7CON(R^{10})$—, $NR^8R^9$—, $NR^8R^9CO$—, $—COOR^8$, heterocyclyl or heterocyclyl$(C_{1-6})$alkyl;
or an adjacent pair of $R^2$, $R^3$, $R^4$, $R^5$ and $R^6$ together with the carbon atoms to which they are attached form an optionally substituted carbocyclic or heterocyclic ring;
$R^7$ is $(C_{1-6})$alkyl or aryl;
$R^8$ and $R^9$ independently represent hydrogen, $(C_{1-6})$alkyl, aryl or aryl$(C_{1-6})$alkyl;

$R^{10}$ is hydrogen or $(C_{1-6})$alkyl; and n is 0, 1, 2, or 3;

or a pharmaceutically acceptable salt thereof.

When a halogen atom is present in the compound of formula (I) it may be fluorine, chlorine, bromine or iodine.

Z preferably represents oxygen.

n is preferably 0 or 1.

X is preferably N and Y is CH.

When n is 1, the group $R^1$ is preferably in the 6- or 8-position, particularly the 8-position.

$R^1$ is preferably halogen e.g. fluoro, or $(C_{1-6})$alkoxy e.g. methoxy. $R^1$ is most preferably fluoro.

When any of $R^1$ to $R^6$ comprise a $(C_{1-6})$alkyl group, whether alone or forming part of a larger group, e.g. alkoxy or alkylthio, the alkyl group may be straight chain, branched or cyclic, it preferably contains 1 to 4 carbon atoms and is most preferably methyl or ethyl.

When any of $R^1$ to $R^6$ comprise a $(C_{2-6})$alkenyl group, whether alone or forming part of a larger group, the alkenyl group may be straight chain, branched or cyclic, it preferably contains 2 to 4 carbon atoms and is most preferably allyl.

Suitable optional substituents for $(C_{1-6})$alkyl, $(C_{2-6})$alkenyl, $(C_{1-6})$alkoxy and $(C_{1-6})$alkylthio groups include one or more substituents selected from halogen e.g. fluoro, $(C_{1-6})$alkoxy e.g. methoxy, hydroxy, carboxy and $(C_{1-6})$alkyl esters thereof, amino, mono- or di-$(C_{1-6})$alkylamino and cyano.

When used herein the term "aryl", whether alone or forming part of a larger group, includes optionally substituted aryl groups such as phenyl and naphthyl, preferably phenyl. The aryl group may have up to 5, preferably 1, 2 or 3 optional substituents. Examples of suitable substituents include halogen, $(C_{1-4})$alkyl e.g. methyl, $(C_{1-4})$haloalkyl e.g. trifluoromethyl, $(C_{1-4})$alkoxy e.g. methoxy, $(C_{1-4})$alkoxy$(C_{1-4})$alkyl e.g. methoxymethyl, hydroxy, carboxy and $(C_{1-6})$alkyl esters thereof, amino, nitro, arylsulphonyl e.g. p-toluenesulphonyl, and $(C_{1-4})$alkylsulphonyl e.g. methanesulphonyl.

When any of $R^2$ to $R^6$ represent heterocyclyl or heterocyclyl$(C_{1-6})$alkyl the heterocyclyl group is preferably a 5- to 10-membered monocyclic or bicyclic ring, which may be saturated or unsaturated, for example containing 1, 2 or 3 heteroatoms selected from oxygen, nitrogen and sulphur; for example pyrrolidine, oxazole, morpholine, pyrimidine or phthalimide. A ring containing one or two nitrogen atoms is preferred. The heterocyclyl group may have to to 5, preferably 1, 2 or 3 optional substituents. Examples of suitable substituents include halogen, $(C_{1-4})$alkyl e.g. methyl, $(C_{1-4})$haloalkyl e.g. trifluoromethyl, $(C_{1-4})$alkoxy e.g. methoxy, $(C_{1-4})$alkoxy$(C_{1-4})$alkyl e.g. methoxymethyl, hydroxy, carboxy and $(C_{1-6})$alkyl esters thereof, amino, nitro, arylsulphonyl e.g. p-toluenesulphonyl, and $(C_{1-4})$alkylsulphonyl e.g. methanesulphonyl.

When an adjacent pair of $R^2$ to $R^6$ together with the carbon atoms to which they are attached form a carbocyclic or heterocyclic ring this is preferably a 5- to 7-membered ring, which may be aromatic or non-aromatic. Heterocyclic rings preferably contain 1, 2 or 3 heteroatoms selected from oxygen, nitrogen and sulphur; for example oxazole, imidazole, thiophene, pyran, dioxan, pyrrole or pyrrolidine. A ring containing one nitrogen atom and one oxygen atom is preferred. It is particularly preferred for the nitrogen to be attached directly to the $R^4$ position. A carbocyclic or heterocyclic ring formed by an adjacent pair of $R^2$ to $R^6$ together with the carbon atoms to which they are attached may be optionally substituted on carbon or nitrogen by one or more substituents, e.g. up to 3 substituents. Examples of suitable substituents include =O, $(C_{1-4})$alkyl e.g. methyl, aryl$(C_{1-4})$alkyl e.g. benzyl or 3-phenylpropyl, aryl e.g. phenyl, $(C_{1-4})$alkoxy e.g. methoxy, $(C_{1-4})$alkoxy$(C_{1-4})$alkyl e.g. methoxymethyl, hydroxy, hydroxy$(C_{1-4})$alkyl e.g. hydroxyethyl, $R^aCO_2-$, $R^aCO_2(C_{1-4})$alkyl e.g. carboethoxypropyl, cyano, cyano$(C_{1-4})$alkyl e.g. 3-cyanopropyl, $R^aR^bN$ and $R^aR^bN(C_{1-4})$alkyl; in which $R^a$ and $R^b$ are independently selected from hydrogen and $(C_{1-4})$alkyl.

A preferred group of compounds are those in which $R^2$ and $R^6$ independently represent hydrogen, halogen, $(C_{1-4})$alkoxy e.g. methoxy, $(C_{1-6})$alkylthio e.g. methyltho, or $NR^8R^9$ wherein $R^8$ and $R^9$ preferably represent $(C_{1-6})$alkyl e.g. dimethylamino, and at least one of $R^2$ and $R^6$ is other than hydrogen; or an adjacent pair of $R^2$ to $R^6$ together with the carbon atoms to which they are attached form an optionally subsituted 5- to 7-membered heterocyclic ring, e.g. a 6- or 7-membered non-aromatic heterocyclic ring or a 5- or 6-membered aromatic heterocyclic ring.

Further preferred groups of compounds are those in which $R^2$, $R^5$ and $R^6$ represent hydrogen, or $R^2$, $R^4$ and $R^6$ represent hydrogen. Another preferred group of compounds are those in which either $R^3$ and $R^4$, or $R^3$ and $R^5$ are other than hydrogen.

A group of compounds according to the invention which may be mentioned are the compounds of formula (Ia):

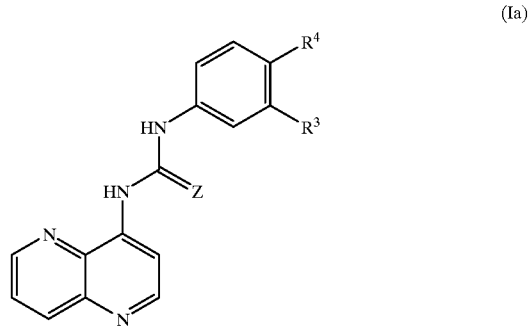

(Ia)

in which:

Z represents oxygen or sulphur;

$R^3$ and $R^4$ independently represent hydrogen, halogen, nitro, cyano, $(C_{1-6})$alkyl, $(C_{1-6})$alkoxy, aryloxy $CF_3O$, $(C_{1-6})$alkylthio, $R^7CO-$, $R^7SO_2NH-$, $R^7CON(R^{10})-$, $NR^8R^9$, $NR^8N^9CO-$, or heterocyclyl;

or $R^3$ and $R^4$ together with the carbon atoms to which they are attached form an optionally substituted carbocyclic or heterocyclic ring;

$R^7$ $(C_{1-6})$alkyl or aryl;

$R^8$ and $R^9$ independently represent hydrogen, $(C_{1-6})$alkyl, aryl or $(C_{1-6})$alkylaryl; and $R^{10}$ hydrogen or $(C_{1-6})$alkyl;

or a pharmaceutically acceptable salt thereof.

Particular compounds according to the invention include those mentioned in the examples and their pharmaceutically acceptable salts.

It will be appreciated that for use in medicine the salts of the compounds of formula (I) should be pharmaceutically acceptable. Suitable pharmaceutically acceptable salts will be apparent to those skilled in the art and include acid addition salts formed with inorganic acids e.g. hydrochloric, hydrobromic, sulphuric, nitric or phosphoric acid; and organic acids e.g. succinic, maleic, acetic, fumaric, citric, tartaric, benzoic, p-toluensulphonic, methanesulphonic or naphthalenesulphonic acid. Other salts e.g. oxalates, may be used, for example in the isolation of compounds of formula (I) and are included within the scope of this invention. Also included within the scope of the invention are solvates and hydrates of comopunds of formula (I).

The invention extends to all isomeric forms including stereoisomers and geometric isomers of the compounds of formula (I) including enantiomers and mixtures thereof e.g. racemates. The different isomeric forms may be separated or resolved by conventional methods, or any given isomer may be obtained by conventional synthetic methods or by stereospecific or asymmetric syntheses.

According to a further feature of the invention there is provided a process for the preparation of compounds of formula (I) and salts thereof which comprises coupling a compound of formula (II):

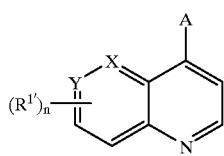

(II)

with a compound of formula (III):

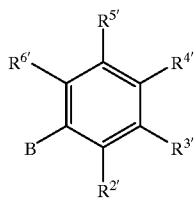

(III)

wherein A and B are appropriate functional groups to form the —NHCONH— or —NHCSNH— moiety when coupled; n X, and Y are as defined in formula (I); and $R^1$ to $R^6$ are $R^1$ to $R^6$ as defined in formula (I) or groups convertible thereto; and thereafter optionally and as necessary and in any appropriate order, converting any $R^1$ to $R^6$ when other than $R^1$ and $R^6$ respectively to $R^1$ to $R^6$, and/or forming a pharmaceutically acceptable salt.

Suitable examples of groups A and B are;
(i) A and B are —NH$_2$
(ii) one of A and B is —CON$_3$ and the other is —NH$_2$
(iii) one of A and B is —CO$_2$H and the other is —NH$_2$
(iv) one of A and B is —N═C═O and the other is —NH$_2$
(v) one of A and B is —N═C═S and the other is —NH$_2$
(vi) one of A and B is —NHCOL and the other is —HN$_2$
(vii) one of A and B is halogen and the other is —NHCONH$_2$.

Wherein L is a leaving group such as chloro, bromo, imidazole, or phenoxy or phenylthio optionally substituted for example with halogen, e.g. chlorine.

when A and B are both —NH$_2$, the reaction is generally effected in the presence of a urea coupling agent such as carbonyldiimidazole.

When one of A and B is —CO$_2$H and the other is —NH$_2$ the reaction is generally effected in the presence of an agent such as diphenylphosphoryl azide and in the presence of a base such as triethylamine.

When one of A and B is —N═C═O or —N═C═S and the other is —NH$_2$ the reaction is suitable carried out in an inert solvent e.g. dimethylformamide or dichloromethane and/or toluene at ambient or elevated temperature, preferably ambient.

When one of A and B is —CON$_3$ or —CO$_2$H and the other is —NH$_2$ the reaction is suitably carried out in an inert solvent e.g. toluene or dimethylformamide at elevated temperature.

When one of A and B is —NHCOL and the other is —NH$_2$ the reaction is suitably carried out in an inert solvent e.g. dichloromethane at ambient temperature, optionally in the presence of a base e.g. triethylamine; or in dimethylformamide at ambient or elevated temperature.

When one of A and B is halogen and the other is —NHCONH$_2$ the reaction is suitable carried out in an inert solvent e.g. toluene, at elevated temperature, optionally in the presence of base.

Suitable examples of compounds having groups $R^1$ to $R^6$ which are convertible to $R^1$ to $R^6$ respectively include compounds where one or more of $R^2$ to $R^6$ are OH and NH$_2$, and compounds where an adjacent pair of $R^2$ to $R^6$ together with the carbon atoms to which they are attached represent a fused pyrrole ring which is unsubstituted on nitrogen, in this case treatment with a base e.g. sodium hydride, and reaction with an electrophile e.g. methyl iodide, benzyl chloride or benzensulfonyl chloride, affords the corresponding subbstituent on the pyrrole nitrogen.

Compounds of formulae (II) and (III) where A and B is —NH$_2$, —N═C═S or halogen are known compounds or can be prepared analogoulsy to known compounds.

Compounds of formulae (II) and (III) where A or B is —N═C═O may be prepared by treating a compound of formula (II) in which:
(i) A or B is amino, with phosgene or a phosgene equivalent, in the presence of excess base or an inert solvent;
(ii) A or B is acylazide (i.e. —CON$_3$), via the nitrene, by thermal rearrangement using conventional conditions (ref. L. S. Trifonov et al, Helv. Chim. Acta, 1987, 70, 262); or
(iii) A or B is —CONH$_2$, via the nitrene intermediate using conventional conditions.

Compounds of formulae (II) and (III) where A or B is —NHCOL may be prepared by reacting a compound of formula (II) or (III) in which A or B is —NH$_2$ with phosgene or a phosgene equivalent, in an inert solvent, at low temperature, if necessary in the presence of a base e.g. triethylamine.

Examples of phosgene equivalents include triphosgene, carbonyldiimidazole, phenyl chloroformate and phenyl chlorothioformate.

Compounds of formulae (II) and (III) where A or B is —NHCONH$_2$ can be prepared from compounds of formulae (II) and (III) where A or B is —NH$_2$ by reaction with an isocyanate under conventional conditions.

The compounds of formula (I) may be prepared singly or as compound libraries comprising at least 2, e.g. 5 to 1000, preferably 10 to 100 compunds of formula (I). Compound libraies may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I), or pharmaceutically acceptable salts thereof.

Novel intermediates of formulae (II) and (III) are also part of this invention.

According to a further aspect of the invention there is provided a compound of formula (II):

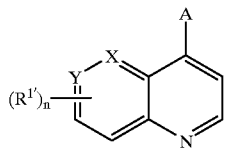

(II)

wherein A is —CON$_3$, —NH$_2$, —CO$_2$H, —N=C=O, —N=C=S, —NHCOL, —NHCONH$_2$ or halogen; L is a leaving group; n, X and Y are as defined in formula (I); and R$^1$ and R$^{1'}$ as defined in formula (I) or a group convertible thereto.

Pharmaceutically acceptable salts may be prepared conventionally by reaction with the appropriate acid or acid derivative.

The compounds of formula (I) and their pharmaceutically acceptable salts are useful for the treatment of diseases or disorders where an antagonist of a human orexin receptor is required such as obesity and diabetes; prolactinoma; hypoprolactinemia; hypothalamic disorder of growth hormone deficiency; idiopathic growth hormone deficiency; Cushing syndrome/disease; hypothalamic-adrenal dysfunction; dwarfism; sleep disorders; sleep apnea; narcolepsy; insomnia; parasomnia; jet-lag syndrome; sleep disturbances associated with diseases such as neurological disorders, neuropathic pain and restless leg syndrome; heart and lung diseases; depression; anxiety; addictions; obsessive compulsive disorder; affective neurosis/disorder; depressive neurosis/disorder; anxiety neurosis; dysthymic disorder; behavior disorder; mood disorder; sexual dysfunction; psychosexual dysfunction; sex disorder; sexual disorder; schizophrenia; manic depression; delerium; dementia; bulimia; and hypopituitarism.

The compounds of formula (I) and their pharmaceutically acceptable salts are particularly useful for the treatment of obesity, including obesity associated with Type 2 diabetes, and sleep disorders.

Others diseases or disorders which may be treated in accordance with the invention include disturbed biological and ciradian rhythms; adrenohypophysis disease; hypophysis disease; hypophysis tumor/adenoma; adrenohypophysis hypofunction; functional or psychogenic amenorrhea; adrenohypophysis hyperfunction; migraine; hyperalgesia; pain; enhanced or exaggerated sensitivity to pain such as hyperalgesia, causalgia and allodynia; acute pain; burn pain; atypical facial pain; neuropathic pain; back pain; complex regional pain syndromes I and II; arthritic pain; sports injury pain; pain related to infection e.g. HIV, post-polio syndrome and post-herpetic neuralgia; phantom limb pain; labour pain; cancer pain; post-chemotherapy pain; post-stroke pain; postoperative pain; neuralgia; and tolerance to narcotics or withdrawal from narcotics.

The invention also provides a method of treating or preventing diseases or disorders where an antagonist of a human orexin receptor is required, which comprises administering to a subject in need thereof an effective amount of a compound of formula (I), or a pharmaceutically acceptable salt thereof.

The invention also provides a compound of formula (I), or a pharmaceutically acceptable salt thereof, for use in the treatment or prophylaxis of diseases or disorders where an antagonist of a human orexin receptor is required.

The invention also provides the use of a compound of formula (I), or a pharmaceutically acceptable salt thereof, in the manufacture of a medicament for the treatment or prophylaxis of diseases or disorders where an antagonist of a human orexin receptor is required.

For use in therapy the compounds of the invention are usually administered as a pharmaceutical composition. The invention also provides a pharmaceutical composition comprising a compound of formula (I), or a pharmaceutically acceptable salt thereof, and a pharmaceutically acceptable carrier.

The compounds of formula (I) and their pharmaceutically acceptable salts may be administered by an convenient method, e.g. by oral, parenteral, buccal, sublingual, nasal, rectal or transdermal administration, and the pharmaceutical compositions adapted accordingly.

The compounds of formula (I) and their pharmaceutically acceptable salts which are active when given orally can be formulated as liquids or solids, e.g. as syrups, suspensions, emulsions, tablets, capsules or lozenges.

A liquid formulation will generally consist of a suspension or solution of the active ingredient in a suitable liquid carrier(s) e.g. an aqueous solvent such as water, ethanol or glycerine, or a non-aqueous solvent, such as polyethylene glycol or an oil. The formulation may also contain a suspending agent, preservative, flavouring and/or colouring agent.

A composition in the form of a tablet can be prepared using any suitable pharmaceutical carrier(s) routinely used for preparing solid formulations, such as magnesium stearate, starch, lactose, sucrose and cellulose.

A composition in the form of a capsule can be prepared using routine encapsulation procedures, e.g. pellets containing the active ingredient can be prepared using standard carriers and then filled into a hard gelatin capsule; alternatively a dispersion or suspension can be prepared using any suitable pharmaceutical carrier(s), e.g. aqueous gums, celluloses, silicates or oils and the dispersion or suspension then filled into a soft gelatin capsule.

Typical parenteral compositions consists of a solution or suspension of the active ingredient in a sterile aqueous carrier or parenterally acceptable oil, e.g. polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active ingredient in a pharmaceutically acceptable aqueous or non-aqueous solvent and are usually presented in single or multidose quantities in sterile form in a sealed container which can take the form of a cartridge or refill for use with an atomising device. Alternatively the sealed container may be a disposable dispensing device such as a single dose nasal inhaler or an aerosol dispenser fitted with a metering valve. Where the dosage form comprises an aerosol dispenser, it will contain a propellant which can be a compressed gas e.g. air, or an organic propellant such as a flurochlorohydrocarbon or hydrofluorocarbon. Aerosol dosage forms can also take the form of pump-atomoisers.

Compositions suitable for buccal or sublingual administration include tablets, lozenges and pastilles where the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

The dose of the compound of formula (I), or a pharmaceutically acceptable salt thereof, used in the treatment or prophylaxis of the abovementioned disorders or diseases will vary in the usual way with the particular disorder or disease being treated, the weight of the subject and other similar factors. However, as a general rule, suitable unit dose may be 0.005 to 1000 mg, more suitably 0.05 to 500 mg. Unit doses may be administered more than once a day for example two or three times a day, so that the total daily dosage is in the range of about 0.01 to 100 mg/kg; and such therapy may extend for a number of weeks or months. In the case of pharmaceutically acceptable salts the above figures are calculated as the parent compound of formula (I).

No toxicological effects are indicated/expected when a compound of formula (I) is administered in the above mentioned dosage range.

Human orexin-A has the amino acid sequence:

```
pyroGlu Pro Leu Pro Asp Cys Cys Arg Gln Lys Thr Cys Ser Cys Arg Leu
1               5                   10                  15
Tyr Glu Leu Leu His Gly Ala Gly Asn His Ala Ala Gly Ile Leu Thr
            20                  25                  30
Leu-NH2
```

Orexin-A can be employed in screening procedures for compounds which inhibit the ligand's activation of the orexin-1 receptor.

In general, such screening procedures involve providing appropriate cells which express the orexin-1 receptor on their surface. Such cells include cells from mammals, yeast, Drosophilia or *E. coli*. In particular, a polynucleotide encoding the orexin-1 receptor is used to transfect cells to express the receptor. The expressed receptor is then contacted with a test compound and an orexin-1 receptor ligand to observe inhibition of a functional response. One such screening procedure involves the use of melanophores which are transfected to express the orexin-1 receptor, as described in WO 92/01810.

Another screening procedure involves introducing RNA encoding the orexin-1 receptor into *Xenopus oocytes* to transiently express the receptor. The receptor oocytes are then contacted with a receptor ligand and a test compound, followed by detection of inhibition of a signal in the case of screening for compounds which are thought to inhibit activation of the receptor by the ligand.

Another method involves screening for compounds which inhibit activation of the receptor by determining inhibition of binding of a labelled orexin-1 receptor ligand to cells which have the receptor on their surface. This method involves transfecting a eukaryotic cell with DNA encoding the orexin-1 receptor such that the cell expresses the receptor on its surface and contacting the cell or cell membrane preparation with a compound in the presence of a labelled form of an orexin-1 receptor ligand. The ligand may contain a radioactive label. The amount of labelled ligand bound to the receptors is measured, e.g. by measuring radioactivity.

Yet another screening technique involves the use of FLIPR equipment for high throughput screening of test compounds that inhibit mobilisation of intracellular calcium ions, or other ions, by affecting the interaction of an orexin-1 receptor ligand with the orexin-1 receptor.

All publications, including but not limited to patents and patent applications, cited in this specification are herein incorporated by reference as if each individual publication were specfically and individually indicated to be incorporated by reference herein as though fully set forth.

The following Examples illustrate the preparation of pharmacologically active compounds of the invention. The Descriptions D1–D10 illustrate the preparation of intermediates to compounds of the invention.

In the Examples $^1$H NMR's were measured at 250 MHz in $d_6$-DMSO unless otherwise stated. All hydrochloride salts unless otherwise stated were prepared by dissolving/ suspending the free-base in methanol and treating with an excess of etheral HCl (1M).

Description 1

4-Chloro-[1,5]naphthyridine

4-Hydroxy-[1,5]naphthyridine-3-carboxylic acid (14.00 g. Joe T. Adams et al., *J.Amer.Chem.Soc.*, 1946, 68, 1317) in quinoline (150 ml) was heated at reflux under argon for 1 h. The reaction mixture was cooled to room temperature then poured onto diethyl ether (500 ml). The precipitated crude 4-hydroxy-[1,5]naphthyridine was collected by filtration, washed with diethyl ether (4×300 ml) and dried in vacuo. A sample of the solid (5.00 g) was heated in phosphorus oxychloride (100 ml) at 115° C. for 1 h. The reaction mixture was cooled to room temperature and the resulting black oil treated with crushed ice with ice-salt bath cooling. The mixture was basified with 0.880 ammonia, then filtered through kieselguhr, washing with ethyl acetate. The organic phase of the filtrate was separated and the aqueous residues washed with ethyl acetate. The combined organics were washed with saturated aqueous sodium chloride and dried ($Na_2SO_4$). Removal of the solvent under reduced pressure afforded the title compound as a waxy yellow solid (1.90 g).

$^1$H NMR (CDCl$_3$) δ: 7.74 (2H, m), 8.46 (1H, dd, J=2+9 Hz), 8.87 (1H, d, J=5 Hz), 9.11 (1H, dd, J=2+4 Hz).

m/z (API$^+$): 165, 167 (MH$^+$).

Description 2

4-Amino-[1,5]naphthyridine

A solution of D1 (1.90 g) in pyridine (80 ml) was treated with n-propylamine hydrochloride (5.59 g) and the mixture heated in reflux under argon 5 h. The reaction mixture was cooled and the pyridine removed under reduced pressure. The residue was treated with aqueous sodium hydroxide (10%) and the resulting solution extracted with diethyl ether. The combined organics were dried ($Na_2SO_4$) and the solvent removed under reduced pressure to give a sticky solid. Trituration with pentane afforded the title compound as a dark yellow solid (1.39 g).

$^1$H NMR (CDCl$_3$) δ: 5.54 (2H, bs), 6.74 (1H, d, J=5 Hz), 7.58 (1H, dd, J=4+8 Hz), 8.25 (1H, dd, J=2+8 Hz), 8.53 (1H, d, J=5 Hz), 8.75 (1H, dd, J=2+4 Hz).

m/z (API$^+$): 146 (MH$^+$).

Description 3

4-Hydroxy-[1,6]naphthyridine-3-carboxylic acid ethyl ester

4-Aminopyridine (15.84 g) and diethyl ethoxymethylenemalonate (34.3 ml) were heated at 110° C. then allowed to stand for 16 h at room temperature. The resulting solid was collected by filtration, washed wtih diethyl ether then pentane and dried in vacuo. A sample of the resulting enamine (10.0 g) was added portionwise to refluxing Dowtherm A (400 ml ). After heating for a further 0.25 h the reaction mixture was cooled then diluted with pentane (400 ml). The precipitated solid was collected by filtration and washed wtih diethyl ether to afford the title compound as a beige solide (3.84 g).

$^1$H NMR δ: 1.29 (3H, t, J=7 Hz), 4.23 (2H, q, J=7 Hz), 7.53 (1H, d, J=6 Hz), 8.64 (1H, s), 8.68 (1H, d, J=6 Hz), 9.25(1H, s), 12.5 (1H, bs).

m/z (API$^+$): 219 (MH$^+$).

Description 4

4-Hydroxy-[1,6]naphthyridine-3-carboxylic acid

D3(7.50 g) in 10% aqueous sodium hydroxide (115 ml) was heaated at reflux for 1.5 h. The reaction mixture was cooled then acidifed with glacial acetic acid. The preciptated solid was collected by filtration and washed with water. Drying in vacuo afforded the title compound as a beige solid (6.41 g).

$^1$H NMR δ: 7.72 (1H, dd, J=1+6 Hz), 8.84 (1H, d, J=6 Hz), 9.3 (1H, s), 9.46 (1H, s), 13.55 (1H, bs), 14.70 (1H, bs).

m/z (API$^+$): 191 (MH$^+$).

Description 5

4-Chloro-[1,6]naphthyridine

D4 (6.3 g) was decarboxylated and a sample (2.00 g) converted to the title compound (0.76 g) by treatment with phosphourus oxychloride as in Description 1.

$^1$H NMR (CDCl$_3$) δ: 7.60 (1H, d, J=5 Hz), 7.95 (1H, d, J=6 Hz), 8.86 (1H, d, J=6 Hz), 8.97 (1H, d, J=5 Hz), 9.68 (1H, s).

m/z (API$^+$): 165, 167 (MH$^+$).

Description 6

4-Amino-[1,6]naphthyridine

A solution of D5 (0.700 g) in pyridine (20 ml) was treated with n-propylamine hydrochloride (2.064 g) and the mixture heated at reflux for 16 h. The reaction mixture was cooled and partitioned between water and ethyl acetate. The aqueous phase was washed with ethyl acetate, the combined organics dried (Na$_2$SO$_4$) and the solvent removed under reduced pressure. Trituration with pentane afforded the title compound as a brown solid (0.100 g).

$^1$H NMR (CDCL$_3$) δ: 5.12 (2H, bs), 6.66 (1H, d, J=5 Hz), 7.78 (1H, d, J=6 Hz), 6.66 (2H, m), 9.24 (1H, s).

m/z (API$^+$): 146 (MH$^+$).

In addition, a sample of the hydrochloride salt (0.200 g) of the title compound was isolated from the aqueous phase obtained on work-up.

$^1$H NMR δ: 6.91 (1H, d, J=7 Hz), 7.83 (1H, d, J=6 Hz), 8.48 (1H, d, J=7 Hz), 8.84 (1H, d, J=6 Hz), 9.65 (2H, bs), 9.85 (1H,s).

m/z (API$^+$): 146 (MH$^+$).

Description 7

4-Hydroxy-6-methoxy-[1,5]naphthyridine-3-carboxylic acid ethyl ester

3-Amino-6-methoxypyridine (12.41 g) and diethyl ethoxymethylene malonate (20.2 ml) in Dowtherm A (400 ml) was heated at reflux, under argon for 1 h. The cooled reaction mixture was poured onto pentane (1 litre). The precipiated solid was collected by filration, washing with pentane. Drying afforded the title compound (24.78 g, crude).

Description 8

4-Hydroxy-6-methoxy-[1,5]naphthyridine-3-carboxylic acid

D7 (642 mg) was converted to the title compound (542 mg) by treatment with aqueous sodium hydroxide (10%) as in Description 4.

m/z: 221 (MH$^+$).

Description 9

4-Chloro-6-methoxy-[1,5]naphthyridine

D8 (6.82 g) was decarboxylated and a sample (3.87 g) converted to the title compound (3.00 g) by treatment with phosphorus oxychloride as in Description 1.

m/z: 195, 197 (MH$^+$).

Description 10

4-Amino-6-methoxy-[1,5]naphthyridine

D6 (2.00 g) was converted to the title compound by treatment with n-propylamine hydrochloride in pyridine as in Description 2. Purfication by chromatography on silica gel eluting with 5–10% methanol in dichloromethane afforded the title compound as a yellow solid (1.00 g).

$^1$H NMR (CDCl$_3$) δ: 4.05 (3H, s), 5.36 (2H, bs), 6.71 (1H, d, J=5 Hz), 7.08 (1H, d, J=9 Hz), 8.10 (1H, d, J=9 Hz), 8.40 (1H, d, J=5 Hz).

m/z:176 (MH$^+$).

EXAMPLE 1

1-(4-Dimethylaminophenyl)-3-[1,5]naphthyridin-4-ylurea dihydrochloride

Method 1

Sodium hydride (0.024 g, 60% in mineral oil) was added to a solution of D2 (0.073 g) in dimethylformamide (5 ml) under argon. The mixture was stirred for 0.5 h then 4-N,N-dimethylaminophenyl isocyanate (0.081 g) added in one portion. The mixture was stirred for 2 h at room temperture then warmed to 80° C. for 1 h. The mixture was cooled to room temperature and added carefully to water (20 ml). The precipitated solid was collected by filtration to give the title compound as the free-base and the hydrochloride salt (0.040 g) was prepared.

$^1$H NMR δ: 3.06 (6H, s), 7.60 (4H, m), 8.15 (1H, dd, J=4+9 Hz), 8.67 (1H, dd, J=1+9 Hz), 8.74 (1H, d, J=6 Hz), 9.07 (1H, d, J=6 Hz), 9.20 (1H, dd, J=1+4 Hz), 10.74 (1H, bs), 10.86 (1H, s).

m/z (API$^+$): 308 (MH$^+$).

Method 2

Sodium hydride (0.96 g, 60% in mineral oil) was added to a solution of D2 (0.292 g) in dimethylformamide (15 ml) under argon. The mixture was stirred for 0.5 h then 4-N,N-dimethylaminophenyl isocyanate (0.324 g) added in one portion. The mixture was stirred for 2 h at room temperature.

The reaction mixture was added carefully to water (20 ml) and extracted with ethyl acetate (3×15 ml). The combined organic phases were washed with water (2×75 ml), dried ($Na_2SO_4$) and the solvent removed at reduced pressue. Chromatography on silica gel eluting with 20–100% ethyl acetate in hexane afforded the the title compound as the free-base. The hydrochloride salt (0.306 g) was prepared. This material was identical spectroscopically with the material from Method 1.

Method 3

A mixture of D2 (0.145 g) and 4-N,N-dimethylaminophenyl isocyanate (0.162 g) in dichloromethane (10 ml) under argon was stirred for 16 h. 4-Dimethylaminopyridine (0.002 g) was added and stirring continued for 2 h. A further portion of the isocyanate (0.100 g) was added and stirring continued for 4 h. The solvent was removed at reduced pressure and the residue triturated with methanol. The solid material was removed by filtration and the filtrate evaporated to dryness. Chromatography on silica gel eluting with 20–100% ethyl acetate in hexane afforded the title compound as the free-base. The hydrochloride salt (0.060 g) was prepared. This material was identical spectroscopically with the material from Method 1.

EXAMPLE 2

1-(4-Methylthiophenyl)-3-[1,5]naphthyridin-4-yl urea hydrochloride

The title compound (0.050 g) was prepared according to the method of Example 1, Method 2 using D2 (0.073 g) and 4-methylthiophenyl isocyanate (0.083 g). The crude reaction mixture was purified by trituration with diethyl ether and the hydrochloride salt was prepared.

$^1$H NMR δ: 2.49 (3H, s), 7.30 (2H, d, J=9 Hz), 7.53 (2H, d, J=9 Hz), 8.14 (1H, dd, J=4+9 Hz), 8.66 (1H, dd, J=1+9 Hz), 8.72 (1H, d, J=7 Hz), 9.05 (1H, d, J=7 Hz), 9.19 (1H, dd, J=1+4 Hz), 10.57 (1H, s), 10.81 (1H, s).

m/z (API$^+$): 311 (MH$^+$).

EXAMPLE 3

1-(4-Dimethylaminophenyl)-3-[1,5]naphthyridin-4-yl thiourea dihydrochloride

The title compound (0.020 g) was prepared according to the method of Example 1, Method 2 from D2 (0.073 g) and 4-N,N-dimethylaminophenyl isothiocyanate (0.089 g). After pouring into water, the precipitated solid was collected by filtration. The solid was dissolved in methanol/dichloromethane, the solution filtered and the filtrate evaporated to dryness. The resulting solid was triturated with diethyl ether to give the title compound as the free-base and the hydrochloride salt was prepared.

$^1$H NMR δ: 3.04 (6H, s), 7.28 (2H, bs), 7.64 (7.65 (2H, bd), 8.16 (1H, dd, J=4+9 Hz), 8.70 (1H, d, J=9 Hz), 9.10 (1H, d, J=7 Hz), 9.19 (1H, bs), 9.61 (1H, d, J=7 Hz), 11.45 (1H, bs), 11.96 (1H, bs).

m/z (API$^+$): 324 (MH$^+$).

EXAMPLE 4

1-(4-Dimethylaminophenyl)-3-[1,5]naphthyridin-4-yl urea

The title compound (0.100 g) was prepared from D6 (0.073 g) and 4-N,N-dimethylaminophenyl isocayanate (0.081 g) according to the method of Example 1, Method 2. Chromatography on silica gel, eluting with 40–100% ethyl acetate in pentane afforded the title compound.

$^1$H NMR δ: 2.67 (6H, s), 6.75 (2H, d, J=9 Hz), 7.35 (2H, d, J=9 Hz), 7.82 (1H, d, J=6 Hz), 8.33 (1H, d, J=5 Hz), 8.72 (1H, d, J=6 Hz), 8.87 (1H, d, J=5 Hz), 8.98 (1H, s), 9.57 (1H, s), 9.64 (1H, s).

m/z (API$^+$): 308 (MH$^+$), 330 (Na adduct).

EXAMPLE 5

1-(1-Methylindol-5-yl)-3-[1,5]naphthyidin-4-yl urea hydrochloride

1-Methyl-5-aminoindole (0.142 g) in dichloromethane (5 ml) was added dropwise to a stirred solution of 1,1'-carbonyldiimidazole (0.157 g) in dichloromethane (5 ml) under argon. The mixture was stirred for 2 h at room temperature and solvent removed at reduced pressure. The residue was dissolved in dimethylformamide (3 ml) and added to a solution of D2 (0.142 g), pretreated for 0.5 h with sodium hydride (0.096 g, 60% in oil), in dimethylformamide (4 ml). The mixture was stirred for 0.5 h at room temperature and at 100° C. for 0.5 h, cooled to room temperature and poured into water (75 ml). The resultant mixture stood at 0° C. overnight then was extracted with ethyl acetate (2×30 ml). The combined organic extracts were washed with water (2×30 ml) then saturated aqueous sodium chloride, dried ($Na_2SO_4$) and the solvent removed at reduced pressure. The residue was column chromatographed on silica gel, eluting with 20–100% ethyl acetate in hexane, to give the title compound as the free-base (0.095 g). The hydrochloride salt (0.065 g) was prepared.

$^1$H NMR δ: 3.79 (3H, s), 6.41 (1H, d, J=3 Hz), 7.26 (1H, d, J=9 Hz), 7.34 (1H, d, J=3 Hz), 7.43 (1H, d, J=9 Hz), 7.84 (1H, s), 8.15 (1H, dd, J=4+9 Hz), 8.67 (1H, d, J=9 Hz), 8.76 (1H, d, J=7 Hz), 9.05 (1H, d, J=7 Hz), 9.20 (1H, d, J=4 Hz), 10.40 (1H, s), 10.85 (1H, s).

m/z (API$^+$): 318 (MH$^+$).

EXAMPLE 6

1-(2-Methylbenzoxazol-6-yl)-3-[1,5]naphthyridin-4-yl urea hydrochloride

A slurry of 2-methyl-6-benzoxazole carboxylic acid (0.953 g) in toluene (100 ml) was treated with triethylamine (0.78 ml) then diphenylphosphoryl azide (1.48 ml). Dimethylformamide (20 ml) was added and the mixture heated at 65° C. for 0.75 h under argon. The reaction mixture was cooled to room temperature and D2 (0.781 g) added. Heating at 65° C. was continued for a further 72 h. The cooled reaction mixture was diluted with ethyl acetate and washed with saturated aqueous sodium carbonate. The organic phase was dried ($Na_2SO_4$) and the solvent removed at reduced pressure to give the free-base of the title compound (crude). The hydrochloride salt was prepared and triturated with cold methanol to give the title compound as a yellow solid (0.920 g).

$^1$NMR δ: 2.61 (3H, s), 7.30 (1H, dd, J=2+9 Hz), 7.63 (1H, d, J=9 Hz), 8.08 (1H, d, J=2 Hz), 8.13 (1H, dd, J=4+9 Hz), 8.62 (1H, dd, J=1+9 Hz), 8.73 (1H, d, J=6 Hz), 9.09 (1H, d, J=6 Hz), 9.19 (1H, dd, J=1+4 Hz), 10.71 (1H,s), 10.79 (1H, s).

m/z (API$^+$): 320 (MH$^+$).

EXAMPLE 7

1-(4-Methyl-3,4-dihydro-2H-benzo[1,4]oxazin-7-yl))-3-[1,5]naphthyridin-4-yl urea dihydrochloride A solution of 1,1-carbonyldiimidazole (0.099 g) in dichloromethane (5 ml) was treated dropwise with a solution of 4-methyl-3,4-dihydro-2H-benzo[1,4]oxazin-7-ylamine (0.100 g) in dichloromethane (5 ml) under argon. After stirring for 2 h at room temperature the solvent was removed at reduced pressure and the residue dissolved in dimethylformamide (5 ml). This was added to a stirring mixture of D2 (0.088 g) and sodium hydride (0.0610 g, 60% dispersion in mineral oil) in dimethylformamide (5 ml). The mixture was stirred at room temperature for 0.5 h then partitioned between water and ethyl acetate. The organic phase was dried ($Na_2SO_4$) and the solvent removed at reduced pressure. Chromatography on silica gel, eluting with 20–60% ethyl acetate in pentane, afforded impure product which was chromoatographed a second time (conditions as above) to give the free-base of the title compund. The hydrochloride salt was prepared and crystallised from methanol to give the title compound (0.011 g).

$^1$H NMR δ: 2.83 (3H, s), 3.23 (2H, bt), 4.28 (2H, bt), 5.69 (bs), 6.75 (1H, d, J=9 Hz), 6.94 (1H, dd, J=2+9 Hz), 7.02 (1H, d, J=2 Hz), 8.16 (1H, dd, J=4+9 Hz), 8.69 (1H, dd, J=1+9 Hz), 8.74 (1H, d, J=6 Hz), 9.05 (1H, d, J=6 Hz), 9.20 (1H, dd, J=1+4 Hz), 10.32 (1H, s), 10.83 (1H, s).

m/z (API$^+$): 336 (MH$^+$).

EXAMPLE 8

1-(2-Methylbenzoxzol-6-yl)-3-[1,6]naphthyridin-4-yl urea hydrochloride

A slurry of 2-methyl-6-benzoxazole carboxylic acid (0.089 g) in tolune (10 ml) was treated wtih triethylamine (0.071 ml) then diphenylphosphoryl azide (0.139 ml) and the mixture heated at 65° C. for 0.7 h under argon. The reaction mixture was cooled to room temperature and D6 (0.091 g) in dimethylformamide (2 ml) and triethylamine (0.071 ml) added. Heating at 65° C. was continued for a further 16 h. The mixture was cooled to room temperature and the solvent removed at reduced pressure. Chromatography on silica gel, eluting wtih 20–100% ethyl acetate in pentane then 1–5% methanol in ethyl acetate afforded the title compound as the free-base. The hydrochloride salt (0.040 g) was prepared.

$^1$H NMR δ: 2.61 (3H, s), 7.32 (1H, dd, J=2+8 Hz), 7.65 (1H, d, J=8 Hz), 8.06 (1H, d, J=2 Hz), 8.10 (1H, d, J=6 Hz), 8.77 (1H, d, J=7 Hz), 8.99 (1H, d, J=6 Hz), 9.13 (1H, d, J=7 Hz), 10.54 (1H, s), 11.42 (1H, s), 11.74 (1H, bs).

m/z (API$^+$): 320 (MH$^+$).

EXAMPLE 9

1-(4-Dimethylaminophenyl)-3-(6-methoxy-[1,5]naphthyridin-4-yl) urea

A mixture of D10 (50 mg), 4-dimethylaminopyridine (2 mg) and 4-dimethylaminophenyl isocyanate (47 mg) in dichloromethane (8 ml) was stirred at room temperature, under argon for 16 h. The solvent was removed under reduced pressure. Chromatography on silica gel eluting with 1–3% methanol in dichloromethane afforded the title compound as a white solid (8 mg).

$^1$H NMR (CDCl$_3$) δ: 2.99 (6H, s), 3.50 (3H, s), 6.40 (1H, bs), 6.75 (1H, d, J=9 Hz), 7.02 (1H, d, J=9 Hz), 7.27 (3H, m), 8.12 (1H, d, J=9 Hz), 8.41 (1H, d, J=5 Hz), 8.64 (1H, d, J=5 Hz), 8.90 (1H, bs).

m/z: 337 (MH$^+$).

Determination of Orexin-1 Receptor Antagonist Activity

The orexin-1 receptor antagonist activity of the compounds of formula (I) was determined in accordance with the following experimental method.

Experimental Method

HEK293 cells expressing the human orexin-1 receptor were grown in cell medium (MEM medium with Earl's salts) containing 2 mM L-Glutamine, 0.4 mg/mL G418 Sulphate from GIBCO BRL and 10% heat inactivated fetal calf serum from Gibco BRL. The cells were seeded at 20,000 cells/100 μl/well into 96-well black clear bottom sterile plates from Costar which had been pre-coated with 10 μg/well of poly-L-lysine from SIGMA. The seeded plates were incubated overnight at 37° C. in 5% $CO_2$.

Agonists were prepared as 1 mM stocks in water:DMSO (1:1). $EC_{50}$ values (the concentration required to produce 50% maximal response) were estimated using 11× half log unit dilutions (Biomek 2000, Beckman) in Tyrode's buffer containing probenecid (10 mM HEPES with 145 mM NaCl, 10 mM glucose, 2.5 mM KCl, 1.5 mM $CaCl_2$, 1.2 mM $MgCl_2$ and 2.5 mM probenecid; pH7.4). Antagonists were prepared as 10 mM stocks in DMSO (100%). Antagonist $IC_{50}$ values (the concentration of compound needed to inhibit 50% of the agonist response) were determined against 3.0 nM human orexin-A using 11× half log unit dilutions in Tyrode's buffer containing 10% DMSO and probenecid.

On the day of assay 50 μl of cell medium containing probenecid (Sigma) and Fluo3AM (Texas Fluorescence Laboratories) was added (Quadra, Tomtec) to each well to give final concentrations of 2.5 mM and 4 μM, respectively. The 96-well plates were incubated for 90 min at 37° C. in 5% $CO_2$. The loading solution containing dye was then aspirated and cells were washed with 4×150 μl Tyrode's buffer containing probenecid and 0.1% gelatin (Denley Cell Wash). The volume of buffer left in each well was 125 μl. Antagonist or buffer (25 μl) was added (Quadra) the cell plates gently shaken and incubated at 37° C. in 5% $CO_2$ for 30 min. Cell plates were then transferred to the Fluorescent Imaging Plate Reader (FLIPR, Molecular Devices) instrument and maintained at 37° C. in humidified air. Prior to drug addition a single image of the cell plate was taken (signal test), to evaluate dye loading consistency. Then run protocol used 60 images taken at 1 second intervals followed by a further 24 images at 5 second intervals. Agonists were added (by the FLIPR) after 20 sec (during continuous reading). From each well, peak fluorescence was determined over the whole assay period and the mean of reading 1–19 inclusive was subtracted from this figure. The peak increase in fluorescence was plotted against compound concentration and iteratively curve fitted using a four parameter logistic fit as described by Bowen and Jerman, TiPS, 1995, 16, 413–417) to generate a concentration effect value. Antagonist Kb values were calculated using the equation:

$$K_b = IC_{50}/(1+([3/EC_{50}]))$$

where $EC_{50}$ was the potency of human orexin-A determined in the assay (in nM terms) and $IC_{50}$ is expressed in molar terms.

As an illustration of the activity of the compounds of formula (I), the compounds of Examples 1 and 2 each had a pKb>7 in this assay.

What is claimed is:

1. A compound of formula (I)

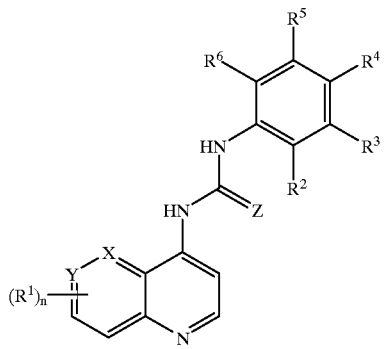

in which:

one of X and Y is N and the other is CH;

Z represents oxygen or sulphur;

$R^1$ represents $(C_{1-6})$alkyl, $(C_{2-6})$alkenyl or $(C_{1-6})$alkoxy, any of which may be optionally substituted; halogen, $R^7CO-$ or $NR^8R^9CO-$;

$R^2$, $R^3$, $R^4$, $R^5$ and $R^6$ independently represent $(C_{1-6})$alkyl, $(C_{2-6})$alkenyl, $(C_{1-6})$alkoxy or $(C_{1-6})$alkythio, any of which may be optionally substituted; hydrogen, halogen, nitro, cyano, aryloxy, aryl($C_{1-6}$)alkyloxy, aryl $(C_{1-6})$alkyl, $R^7CO-$, $R^7SO_2NH-$, $R^7CON(R^{10})-$, $NR^8R^9-$, $NR^8R^9CO-$, $-COOR^8$, heterocyclyl or heterocyclyl($C_{1-6}$)alkyl;

or an adjacent pair of $R^2$, $R^3$, $R^4$, $R^5$ and $R^6$ together with the carbon atoms to which they are attached form an optionally substituted carbocyclic or heterocyclic ring;

$R^7$ is $(C_{1-6})$alkyl or aryl;

$R^8$ and $R^9$ independently represent hydrogen, $(C_{1-6})$alkyl, aryl or aryl($C_{1-6}$)alkyl;

$R^{10}$ is hydrogen or $(C_{1-6})$alkyl; and n is 0, 1, 2 or 3;

or a pharmaceutically acceptable salt thereof.

2. A compound according to claim 1 in which X is N and Y is CH.

3. A compound according to claim 1 in which Z represents oxygen.

4. A compound according to claim 1 in which n is 0 or 1.

5. A compound according to claim 1 in which $R^2$ and $R^6$ independently represent hydrogen, halogen, $(C_{1-6})$alkoxy, $(C_{1-6})$alkythio or $NR^8R^9$, and at least one of $R^2$ to $R^6$ is other than hydrogen; or an adjacent pair of $R^2$ to $R^6$ together with the carbon atoms to which they are attached form an optionally substituted 5- to 7-membered heterocyclic ring.

6. A compound according to claim 1 in which $R^2$, $R^5$ and $R^6$ represent hydrogen, or $R^2$, $R^4$ and $R^6$ represent hydrogen.

7. A process for the preparation of a compound of formula (I) as defined in claim 1 or a salt thereof which comprises coupling a compound of formula (II):

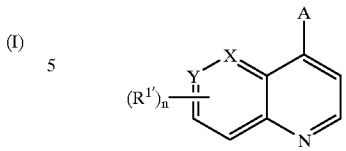

with a compound of formula (III):

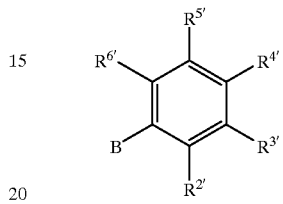

wherein A and B are appropriate functional groups to form the —NHCONH— or —NHCSNH— moiety when coupled; n, X and Y are as defined in formula (I); and $R^1$ to $R^6$ are $R^1$ to $R^6$ as defined in formula (I) or groups convertible thereto; and thereafter optionally and as necessary and in any appropriate order, converting any $R^1$ to $R^6$ when other than $R^1$ and $R^6$ respectively to $R^1$ to $R^6$, and/or forming a pharmaceutically acceptable salt.

8. A pharmaceutical composition comprising a compound of formula (I) as defined in claim 1, or a pharmaceutically acceptable salt thereof, and a pharmaceutically acceptable carrier.

9. A method of treating or preventing diseases or disorders where an antagonist of a human orexin receptor is required, which comprises administering to a subject in need thereof an effective amount of a compound of formula (I) as defined in claim 1, or a pharmaceutically acceptable salt thereof.

10. A method of treating or preventing a diseases or disorder selected from obesity and sleep disorders, which comprises administering to a subject in need thereof an effective amount of a compound of formula (I) as defined in claim 1, or a pharmaceutically acceptable salt thereof.

11. A compound according to claim 1 selected from 1-(4-dimethylaminophenyl)-3-[1,5]naphthyridin-4-yl urea dihydrochloride, 1-(4-methylthiophenyl)-3-[1,5]naphthyridin-4-yl urea hydrochloride, 1-(4-dimethylaminophenyl)-3-[1,5]naphthyridin-4-yl thiourea dihydrochloride, 1-(4-dimethylaminophenyl)-3-[1,6]naphthyridin-4-yl urea, 1-(1-methylindol-5-yl)-3-[1,5]naphthyridin-4-yl urea hydrochloride, 1-(2-methylbenzoxazol-6-yl)-3-[1,5]naphthyridin-4-yl urea hydrochloride, 1-(4-methyl-3,4-dihydro-2H-benzo[1,4]oxazin-7-yl))-3-[1,5]naphthyridin-4-yl urea dihydrochloride, 1-(2-methylbenzoxzol-6-yl)-3-[1,6]naphthyridin-4-yl urea hydrochloride; and 1-(4-dimethylaminophenyl)-3-(6-methoxy-[1,5] naphthyridin-4-yl) urea.

* * * * *